United States Patent [19]

Ryan

[11] Patent Number: 4,472,534

[45] Date of Patent: Sep. 18, 1984

[54] SLURRY PHASE SYNGAS PROCESS

[75] Inventor: Robert C. Ryan, Houston, Tex.

[73] Assignee: Shell Oil Company, Houston, Tex.

[21] Appl. No.: 401,436

[22] Filed: Jul. 23, 1982

[51] Int. Cl.³ .................................................. C07C 1/04
[52] U.S. Cl. ..................................... 518/700; 502/162
[58] Field of Search ......................................... 518/700

[56] References Cited

U.S. PATENT DOCUMENTS 2,775,607 12/1956 Kolbel et al. ......................... 518/700
3,400,163 9/1968 Mason et al. ..................... 568/882 X Primary Examiner—Howard T. Mars
Attorney, Agent, or Firm—Ronald L. Clendenen; Ronald R. Reper

[57] ABSTRACT

Syngas is converted to hydrocarbons with a Fischer-Tropsch catalyst contained in a slurry phase wherein additionally dissolved in the slurry phase is a phosphabicycloalkane.

9 Claims, No Drawings

SLURRY PHASE SYNGAS PROCESS

FIELD OF THE INVENTION

This invention relates to a process for converting syngas to hydrocarbons by contacting the syngas with a Fischer-Tropsch catalyst contained in a slurry phase wherein additionally dissolved in a slurry phase is a phosphabicycloalkane.

BACKGROUND OF THE INVENTION

There are several techniques available for contacting syngas with Fischer-Tropsch catalysts. For example, the catalyst can be contained in a fixed bed or it may be contained in a fluidized bed. Alternatively, the catalyst may be slurried in an inert solvent and the syngas can be bubbled up there through. The use of a slurry phase provides for the possibility for making additions to the slurry phase which will modify the catalytic reactivity of the catalyst without having to directly incorporate these additives in the catalyst per se. For example, these additives may not be easily incorporated into the catalyst or they might be readily leached out of the catalyst by the reaction products, in which case the use of a slurry phase incorporating an inert solvent provides a means for maintaining these additives in the reacting system.

SUMMARY OF INVENTION

The instant invention relates to a process for converting syngas (carbon monoxide and hydrogen) to hydrocarbons, which process comprises contacting the syngas with an iron based Fischer-Tropsch catalyst wherein said catalyst is dispersed as a slurry in an inert organic solvent and wherein additionally, there is dissolved in the solvent a phosphabicycloalkane having the general formula:

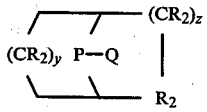

where Q represents hydrogen or non-acetylenic hydrocarbyl of 1 to 36 carbon atoms, y and z represent positive integers whose sum is from 2 to 3, and R represents hydrogen or lower alkyl of 1 to 4 carbons such that no more than two R groups are alkyl at any one time and that each of said alkyl groups is attached to a different ring carbon. The use of the phosphabicycloalkane enhances activity of the catalyst to provide for a higher conversion of a syngas. It further enhances the selectivity of the products to the very useful $C_2$-$C_4$ olefins. These olefins provide very useful feedstocks for other petrochemical processes, e.g. preparation of polymers, preparation of lubricants, etc.

DESCRIPTION OF THE PREFERRED EMBODIMENTS

The instant slurry phase process first involves the addition of the catalyst, ground to a suitable particle size, to an inert solvent to produce a slurry phase and then bubbling syngas through the slurry phase which would prevent the catalyst from settling. Alternatively, mechanical mixing may be provided to maintain the catalyst in the slurry phase and to also improve contact with the syngas.

The catalyst utilized in the instant process are iron-based Fischer-Tropsch catalysts which are well known in the art. More specifically desirable as catalysts for use in the instant process are those iron-based Fischer-Tropsch catalysts containing at least one other transition metal catalytically active species. The catalyst optionally may contain promoter compounds selected from Group 1A (alkali metal), Group 2A (Alkaline earth metals), Group 3A, Group 4A, the rare earth series, and the actinide series. The preferred catalyst for use in the instant process comprises iron, manganese and zinc. The catalysts used herein may either be unsupported or supported on an appropriate, inert support such as for example, aluminam, silica, silica-aluminam, etc. When utilizing the slurry phase, the catalysts are ground to an appropriate size such that they can readily be maintained in the slurry phase. Typically this will be around 100 mesh or smaller.

The preferred catalyst utilized in the present process will contain from about 15 to about 50 percent by weight of iron measured as a metal, and exclusive of any support utilized, from about 15 to about 50 percent by weight of manganese measured as a metal, exclusive of any support utilized, and from about 2 to about 10 percent by weight of zinc, measured as a metal, exclusive of any support utilized. It is understood that reference to the metals in the Fischer-Tropsch catalyst is for purposes of convenience and does not necessarily express the oxidation state thereof. It is understood that the metals will be in various oxidation states and can form very complex compounds with each other and with oxygen.

The inert organic solvent that is utilized to prepare the slurry phase must be one that is inert to the reaction conditions, both with regard to reactants and products. Suitable examples of organic solvents are alkanes, alkenes, alkanols, phenols, benzenes, ethers and siloxanes. Another restriction on the inert organic solvent is that it must be a liquid at the reaction conditions and pressure. For example, a wax with a low melting point which is a solid at room temperature would be satisfactory if it were a liquid at the reaction temperature and pressure.

The critical aspect of the instant invention is the addition of the phosphorous containing compound to the slurry phase to improve the activity of the catalyst. These compounds and their preparation are described in U.S. Pat. No. 3,400,163, patented Sept. 3, 1968, incorporated by reference herein. Generically, these compounds are hydrocarbyl-substituted or unsubstituted monophosphabicycloalkanes of 8 to 9 atoms in which the smallest phosphorus-containing ring contains at least 5 atoms, and the phosphorus atom therein is a member of a bridge linkage but is not a bridgehead atom. In addition to the hydrocarbyl substitution on the phosphorus atom, the ring carbons may also be substituted. However, it is preferred that such C-substituents be limited to nonbulky ones. One class of such compounds has from 7 to 46 carbon atoms, preferably from 12 to 40, and is represented by the formula:

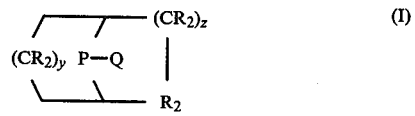   (I)

where Q represents hydrogen or hydrocarbyl, y and z represent positive integers whose sum is from 2 to 3 and each of which has a minimum value of 1, and R represents hydrogen and lower alkyl of from 1 to 4 carbon atoms, such as methyl, ethyl, propyl, and butyl. It is preferred that no more than two R groups be alkyl at any one time and that each of these be attached to a different ring carbon. It is to be understood that in the foregoing graphic formula and those appearing hereinafter the line portion of the structure represents a conventional organic chemical covalent bond with saturated carbon atom at each indicated intersection, the saturation being by the required number of hydrogen atoms or hydrocarbyl radicals.

The term "hydrocarbyl" is used in its accepted meaning as representing a radical formed from a hydrocarbon by removal of a hydrogen atom. The hydrocarbyl groups represented by Q in the formula above may be any non-acetylenic organic radical composed solely of carbon and hydrogen. The widest variation is possible in that the (non-acetylenic) hydrocarbyl group may be alkyl, alkenyl, cycloalkyl, cycloalkenyl, aryl, aralkyl, alkaryl, single ring, multi-ring, straight chain, branched chain, large, or small. Representative hydrocarbyl groups include methyl, ethyl, methallyl, n-butyl, hexenyl, isooctyl, dodecyl, oleyl, octadecyl, eicosyl, hexacosyl, octacosyl, triacontyl, hexatriacontyl, tetracontyl, cyclohexyl, cyclooctyl, cyclooctenyl, phenyl, naphthyl, benzyl, styryl, phenethyl, and the like. Thus, a particularly useful class of bicyclic heterocyclic tert-phospines is that containing only carbon, hydrogen, and phosphorus atoms.

Substituted hydrocarbyl groups are also contemplated and may contain a functional group such as the carbonyl, carboxyl, nitro, amino, hydroxy (e.g. hydroxyethyl), cyano, sulfonyl, and sulfoxyl groups. A particularly useful group of phosphines consists of those in which Q is hydrocarbyl of from 1 to 36 carbon atoms; especially preferred are those in which Q is hydrocarbyl of from 4 to 30 carbons.

Hence, a preferred group of bicyclic heterocyclic tert-phosphines includes those represented by the formula:

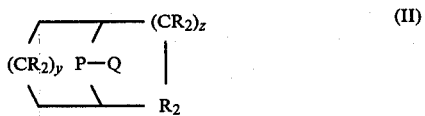

(II)

where Q represents hydrocarbyl of 1 to 36 carbons and especially of 4 to 30, y and z represent positive integers whose sum is from 2 to 3 and each of which has a minimum value of 1, and R is a member selected from the group consisting of hydrogen and alkyl and 1 to 4 carbons such that no more than two R groups be alkyl at any one time and that each of said alkyl groups be attached to a different ring carbon.

It is sometimes desirable to balance the size of the substituents in the aforedescribed phosphines. When the R substituents are relatively large, e.g. butyl, it may be desirable to choose a smaller Q. Conversely, when Q is large, e.g. eicosyl or hexatriacontyl, it may be desirable that the R substituents be smaller and/or less numerous, such as monomethyl or dimethyl. Particularly useful compounds are those in which the sum or R and Q is no greater than 38 carbon atoms and those in which the total number of carbon atoms is no greater than 46.

Similarly, a preferred group of bicyclic heterocyclic secphosphines includes those represented by the foregoing formula (II), but in which Q represents hydrogen.

It will be apparent from the preceding discussion that a variety of substituted and unsubstituted monophosphabicycloalkanes may be produced. In the nomenclature of such compounds, as well as the reactants employed for the production thereof, conventional numbering of the ring systems has been employed, as further illustrated by the following formulas:

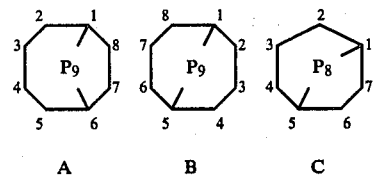

A    B    C

Typical products of the process of the invention, numbered according to this system include 9-phosphabicyclononane in which the smallest P-containing ring contains at least 5 atoms; 9-phosphabicyclo[4.2.1]-nonane; 9-phosphabicyclo([3.3.1]nonane; 9-hydrocarbyl-9-phosphabicyclononane in which the smallest P-containing ring contains at least 5 atoms; 9-hydrocarbyl-9-phosphabicyclo[4.2.1]nonane; 9-aryl-9-phosphabicyclo[4.2.1]-nonane, such as 9-phenyl-9-phosphabicyclo[4.2.1]nonane; (di)alkyl-9-aryl-9-phosphabicyclo[4.2.1]nonane, such as 3,7-dimethyl-9-phenyl-9-phosphabicyclo[4.2.1]nonane and 3,8-dimethyl-9-phenyl-9-phosphabicyclo-[4.2.1]nonane; 9-alkyl-9-phosphabicyclo[4.2.1]nonane, such as 9-octadecyl-9-phosphabicyclo[4.2.1]nonane, 9-hexyl-9-phosphabicyclo[4.2.1]nonane, 9-eicosyl-9-phosphabicyclo[4.2.1]nonane, and 9-triacontyl-9-phosphabicyclo[4.2.1]nonane; 9-cycloalkyl-9-phosphabicyclo[4.2.1]nonane, such as 9-cyclohexyl-9-phosphabicyclo[4.2.1]nonane; 9-hydrocarbyl-9-phosphabicyclo[3.3.1]nonane; 9-aryl-9-phosphabicyclo[3.3.1]nonane, such as 9-pheyl-9-phosphabicyclo[3.3.1]nonane; 9-alkyl-9-phosphabicyclo[3.3.1]-nonane, such as 9-hexyl-9phosphabicyclo[3.3.1]nonane and 9-eicosyl-9-phosphabicyclo[3.3.1]nonane; (di)alkyl-9-aryl-9-phosphabicyclo[3.3.1]nonane, such as 3,7-dimethyl-9-phenyl-9-phosphabicyclo[3.3.1]nonane and 3,8-dimethyl-9-phenyl-9-phosphabicyclo[3.3.1]nonane; 9-cycloalkyl-9-phosphabicyclo[3.3.1]nonane, such as 9-cyclohexyl-9-phosphabicyclo[3.3.1]-nonane; 8-phosphabicyclo[3.2.1]octane; 8-hydrocarbyl-8-phosphabicyclo-[3.2.1]octane; 8-aryl-8-phosphabicyclo[3.2.1]octane, such as 8-phenyl-8-phosphabicyclo[3.2.1]octane; alkyl-8-aryl-8-phosphabicyclo[3.2.1]octane, such as 6-methyl-8-phenyl-8-phosphabicyclo[3.2.1]octane; 8-alkyl-8-phosphabicyclo[3.2.1]octane, such as 8-butyl-8-phosphabicyclo[3.2.1]-octane, 8-eicosyl-8-phosphabicyclo[3.2.1]octane, 8-triacontyl-8-phosphabicyclo[3.2.-1]octane, and 8-octadecyl-8-phosphabicyclo[3.2.1]octane, and the like.

The most preferred additive to be utilized in the slurry phase comprises a mixture of 9-eicocyl-9-phosphabicyclo[4.2.1]nonane and 9-eicocyl-9-phosphabicyclo[3.3.1]nonane. In general, the weight ratio of phosphene compound utilized as an additive and the catalyst will range from about 0.01 to about 0.5, preferably from about 0.05 to about 0.25. The instant slurry phase process is carried out at temperatures ranging from about 175° C. to about 400° C., preferrably from about 200° C.

to about 350° C. Typical reaction pressures range from about 5 to about 500 bar, preferrably from about 5 to about 200 bar, and typical feed rates may include gaseous hourly space velocities ranging from about 500 to about 10,000 1/1/hr. A wide range of carbon monoxide to hydrogen can be used in the feed. For example, a carbon monoxide to hydrogen ratio ranging from about 1:2 to about 3:1 is generally suitable, although other ratios can be utilized. The product of the instant process produces hydrocarbons which comprise primarily alkanes, alkenes and alcohols. There is a high selectivity to the lower carbon numbered compounds, for example carbon numbers ranging from $C_1$ to about $C_{10}$. There is a particularly high selectivity to alkynes having carbon numbers ranging from 2 to about 4.

The process of the instant invention, including preparation of a catalyst composition used therein will be further described below by the following illustriative 325° C. It was then taken into a dry box and crushed to a fine powder (less than 100 mesh) and then put into a 300 ml autoclave. One hundred fifty ml of NEODEN ® 18 (linear $C_{18}$ alpha olefin) was then placed in the reactor. An appropriate amount of the phosphorus containing additive used in the instant invention was added to the autoclave. The autoclave was sealed, flushed with syngas and then brought up to the appropriate reaction temperature and pressure. The reaction temperature was about 275° C. and the reaction pressure was about 900 psig. Hydrogen and carbon monoxide in a ratio of 1:2 were bubbled through the autoclave at approximately 250 GHSV. The results of this experiment are shown as example 1 and Table 1. Example A which is not according to this invention, illstrates the use of triphenylphosphene as an additive. Example B, also not according to this invention illustrates the results obtained when no additive is added.

TABLE I

Slurry Phase Syngas Reactions
Fe/Mn/Zn Catalysts[a] + Additives (A) in NEODENE 18
275° C., 900 psig (1H$_2$:2CO), 2500 GHSV

| Example | Additives (A) (wt %)[b] | % Syngas Conversion | $C_1$ Methane Methanol | $C_2$ Ethene/ Ethane Ethanol | $C_3$ Propane/ Propane Propanol | $C_4$ Butene/ Butane Butanol | $C_2^=$-$C_4^=$ | $C_5^+$ |
|---|---|---|---|---|---|---|---|---|
| 1 | RM-17[c] 19.3 | 38.2 | 11.6 1.7 | 8.9 5.1 1.0 | 8.0 3.7 0.4 | 19.3 7.1 0.3 | 53.87 | 32.9 |
| A | Pφ$_3$ 10.6 | 15.9 | 6.1 1.3 | 9.5 2.5 0.8 | 0.0 0.4 3.0 | 10.3 10.3 0.7 | 37.5 | 55.0 |
| B | — | 18.2 | 6.9 0.7 | 9.8 0.3 0.6 | 0.0 1.8 0.1 | 18.7 9.8 0.6 | 41.7 | 50.6 |

[a]Catalyst compositions: 25 wt % Fe, 25 wt % Mn, 3 wt % Zn.
[b]Wt % of additive is based on amount of catalyst.
[c]A mixture of 9-eicosyl-9-phosphabicyclo[4.2.1]nonane and 9-eicosyl-9-phosphabicyclo[3.3.1]nonane.

embodiments which are provided for illustration and are not to be construed as limiting the invention.

ILLUSTRATIVE EMBODIMENTS

The following example illustrates the typical preparation of a catalyst utilized in the instant process. One hundred eighty grams of Fe(NO$_3$)$_2$·9H$_2$O, 160 grams of Mn(NO$_3$)$_2$(50% solution) and 13 grams of Zn(NO$_3$)$_2$ were placed in a 2 liter beaker to which was added sufficient distilled water to bring the total volume to 1 liter. A one molar solution of sodium carbonate was prepared by placing 159 grams of sodium carbonate in 1.5 liters of distilled water in a 2 liter beaker.

The contents of both beakers were heated to 85° C. and then added to separatory funnels. The solutions were added to a 4 liter beaker containing 800 ml of distilled water at 65° C. The solutions were added at a rate such that a pH of 6.5 was maintained in the 4 liter beaker. After addition, the resultant material was heated to 85° C. and held for 20 minutes.

Solution was filtered, while hot, in a large Buchner funnel. The residue was reslurried with 1.5 liter of warm water and filtered again. The reslurry procedure was repeated ten times.

The residue remaining after final filtration was dried in a vacuum oven at 125° C. and 20 inches overnight and then calcined at 300° C. for 4 hours.

The following illustrates the process of the instant invention. Approximately 15 ml (20-30 mesh) of the catalyst prepared as described above was first placed in a glass tube and reduced under hydrogen for 20 hours at Other inert organic compounds such as silicon oil, mineral oil, and NEODOL ® 25-3T ($C_{12}$-$C_{15}$ ethoxylated linear alcohol having approximately 3 moles of EO per mole of alcohol) were found to be suitable for preparing the slurry phase.

I claim:
1. A process for converting carbon monoxide and hydrogen to hydrocarbons which comprises contacting the carbon monoxide and hydrogen at a temperature ranging from about 175° C. to about 400° C. and a pressure ranging from about 5 bar to about 500 bar with an iron-based Fischer-Tropsch catalyst wherein said catalyst is dispensed as a slurry in an inert organic solvent and wherein additionally is dissolved in the solvent a phosphabicycloalkane having the formula:

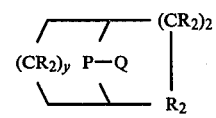

where Q represents hydrogen or non-acetylenic hydrocarbyl of 1 to 36 carbon atoms y and z represent positive integers whose sum is from 2 to 3, and R represents hydrogen or lower alkyl of 1 to 4 carbons such that no more than two R groups are alkyl at any one time and that each of said alkyl groups is attached to a different ring carbon.

2. The process of claim 1 wherein the Fischer-Tropsch catalyst comprises iron and at least one other transition metal.

3. The process of claim 2 wherein the catalyst comprises iron, manganese and zinc.

4. The process of claim 3 wherein the concentration of the iron ranges from about 15 to about 50 percent by weight measured as the metal exclusive of any support, the manganese ranges from about 15 to about 50 percent by weight measured as the metal, exclusive of any support and the zinc ranges from about 2 to about 10 percent by weight measured as the metal exclusive of the support.

5. The process of claim 1, 2, 3 or 4 wherein the temperature ranges from about 200° C. to about 350° C. and the pressure ranges from about 5 bar to about 200 bar.

6. The process of claims 1, 2, 3 and 4 wherein the inert solvent is selected from the group consisting of alkanes, alkenes, alkanols, siloxanes and mixtures thereof which are liquid at the contacting temperatures and pressures.

7. The process of claims 1, 2, 3 and 4 wherein the weight ratio of phosphabicycloalkane to catalyst range from 0.01 to about 0.5.

8. The process of claims 1, 2, 3 or 4 wherein the weight ratio of phosphabicycloalkane to catalyst ranges from about 0.05 to about 0.25.

9. The process of claims 1, 2, 3 or 4 wherein the phosphabicycloalkane is selected from the group consisting of 9-eicosyl-9-phosphabicyclo[4.2.1]nonane, 9-eicosyl-9-phosphabicyclo[3.3.1]nonane and mixtures thereof.

* * * * *